United States Patent [19]

Haack

[11] Patent Number: 4,917,603
[45] Date of Patent: Apr. 17, 1990

[54] DENTAL ISOLATION SYSTEM

[76] Inventor: August F. Haack, 3813 Don Juan Ct, NW, Albuquerque, N. Mex. 87107

[21] Appl. No.: 302,774

[22] Filed: Jan. 30, 1989

[51] Int. Cl.$^4$ .............................................. A61C 1/00
[52] U.S. Cl. ....................................... 433/29; 433/84; 433/91
[58] Field of Search ........................ 433/29, 80, 91, 84

[56] References Cited

U.S. PATENT DOCUMENTS

| | | | |
|---|---|---|---|
| 4,045,874 | 9/1977 | Roman | 433/29 |
| 4,106,501 | 8/1978 | Ozbey et al. | 433/80 X |
| 4,340,365 | 7/1982 | Pisanu | 433/91 X |
| 4,560,351 | 12/1985 | Osborne | 433/80 |
| 4,589,846 | 5/1986 | Annoni | 433/30 |
| 4,611,992 | 9/1986 | Lokker | 433/80 X |
| 4,727,416 | 2/1988 | Cooper et al. | 433/29 X |

Primary Examiner—John J. Wilson
Assistant Examiner—Nicholas D. Lucchesi

[57] ABSTRACT

A system is implemented to isolate the patient and dentist from the breakdown products of tooth drilling including toxic mercury vapor generated during amalgam removal. The system includes a tooth isolation assembly, a fiber optic illumination and viewing system, a gas and water evacuation method and a compressed air optical surface clearing system.

1 Claim, 2 Drawing Sheets

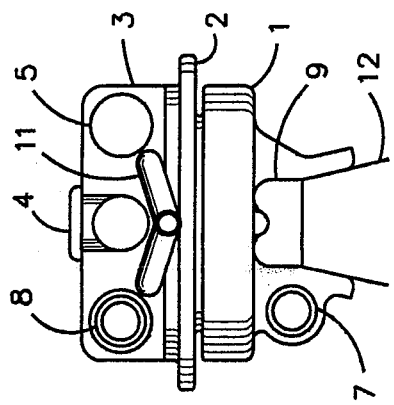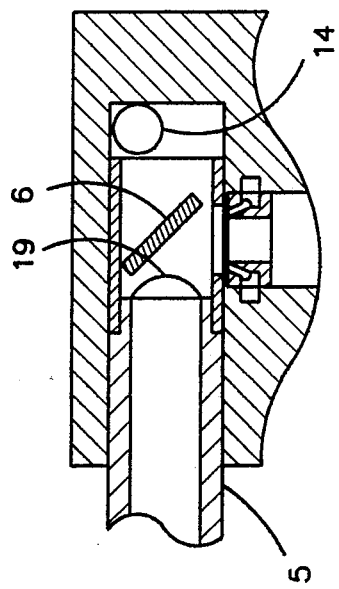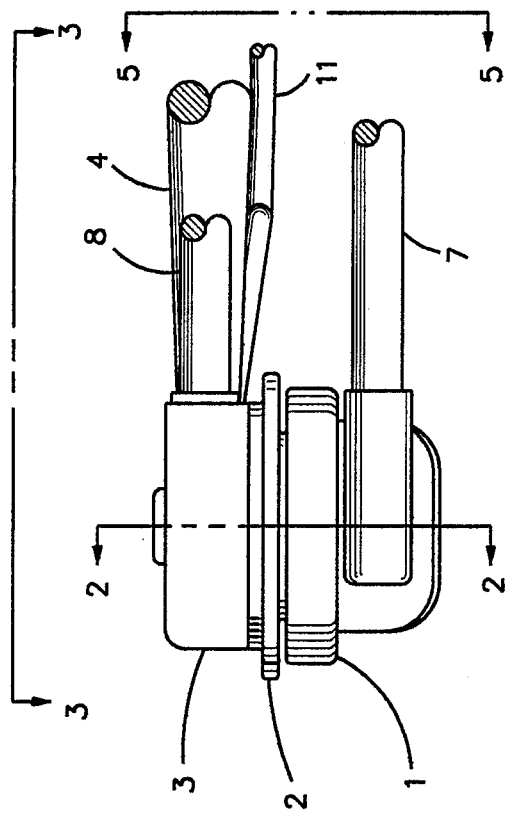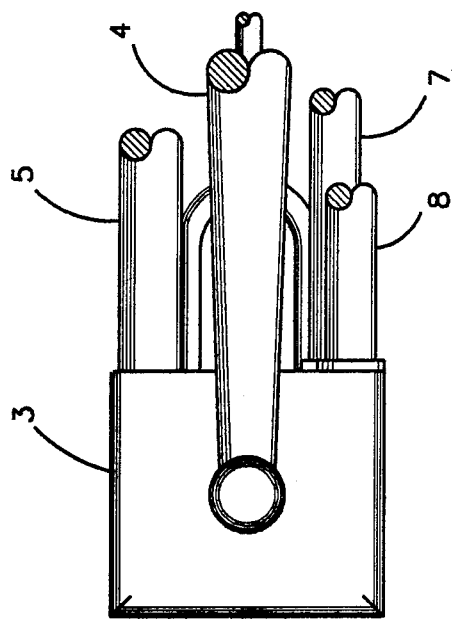

DENTAL ISOLATION SYSTEM

FIELD OF INVENTION

This invention is applicable to dental tooth drilling operations, i.e., the removal of decay, amalgams and other materials.

CROSS REFERENCE TO RELATED APPLICATIONS

None.

DISCUSSION OF PRIOR ART

The current methods of dental drilling operations expose the patient and the dentist to the breakdown products of drilling to various degrees. The most toxic of these products is mercury vapor which is generated during the removal of amalgams. Mercury accumulation in the body has been associated with various diseases. Current isolation techniques include placing rubber dams in the mouth which are effective in keeping solid particles from contacting the surfaces of the mouth but which do not prevent the gaseous breakdown products from contacting these as well as being inhaled by the patient and the dentist. Nose breathing apparatus provides some degree of protection for the patient, but is inherently imperfect since gaseous products can enter the nose through the back of the mouth. Hoods are used by some dentists which have air circulation systems to quickly remove vapors emanating from the patient's mouth to minimize the buildup of high concentrations about the head.

No devices are known to exist which completely isolate both the patient and the dentist from gaseous and particulate breakdown products inherent in dental drilling operations.

OBJECTS

Accordingly, the object of my invention is to isolate both the patient and the dentist as perfectly as is possible from the gaseous and particulate breakdown products generated during dental drilling operations.

Further objects and advantages of my invention will become apparent from a consideration of the drawings and ensuing description thereof.

BRIEF DESCRIPTION OF THE DRAWINGS

FIG. 3 is a top view of the Tooth Isolation Assembly taken from FIG. 4 as shown by 3—3.

FIG. 4 is a side view of the Tooth Isolation Assembly.

FIG. 5 is an end view of the Tooth Isolation Assembly taken from FIG. 4 as shown by 5—5, looking along a row of teeth.

FIG. 6 is a cross section view of the end of the fiber optic assembly taken from FIG. 2 as shown by 6—6.

Figure 1:
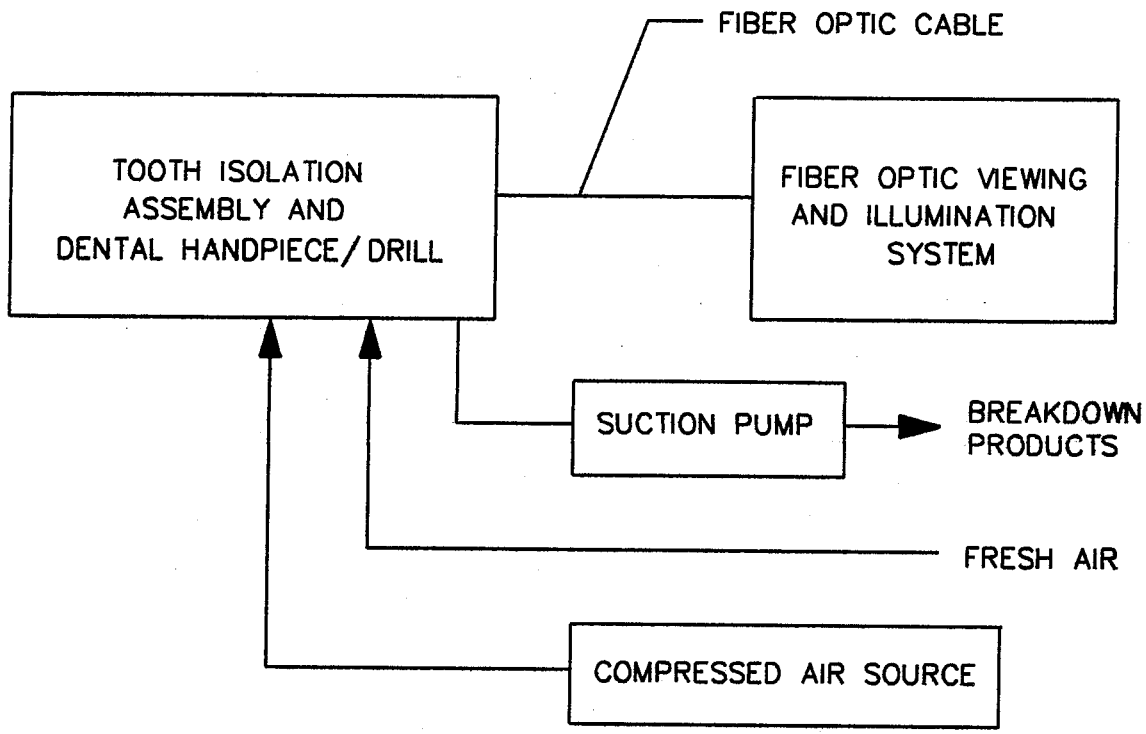
FIG. 1 is a schematic drawing of the Dental Isolation System.

LIST OF REFERENCE NUMERALS 1 cap
2 bellows
3 manifold
4 handpiece
5 fiber optic cable
6 right angle mirror
7 cap hose
8 manifold hose
9 tooth
10 drill
11 tubes
12 gums
13 nozzle ring
14 hole of 3
15 left hand cavity of 3
16 nozzle hole of 13
17 tapered seal of 1 and 2
18 right hand cavity of 3
19 fiber optic lens of 5
20 tip of 5

DESCRIPTION OF THE PREFERRED EMBODIMENT

Referring to schematic FIG. 1: The Dental Isolation System consists of the Tooth Isolation Assembly mated to a Dental Handpiece/Drill; a Fiber Optic Viewing and Illumination System which is attached to the Tooth Isolation Assembly; a Suction Pump, a Fresh Air supply and a Compressed Air Source which are connected to the Tooth Isolation Assembly by means of flexible tubing. The Tooth Isolation Assembly and Dental Handpiece/Drill are placed over the tooth which thus isolates the patient and dentist from the breakdown products of drilling. These products are removed through flexible tubing by means of a suction pump and replaced with fresh air. During the drilling operation, a view of the tooth is provided by means of the Fiber Optic Viewing and Illumination System. The surfaces of the optics are kept free of debris and water, which is used to cool the tooth during drilling, by means of air jets derived from the Compressed Air Supply.

Figure 2:
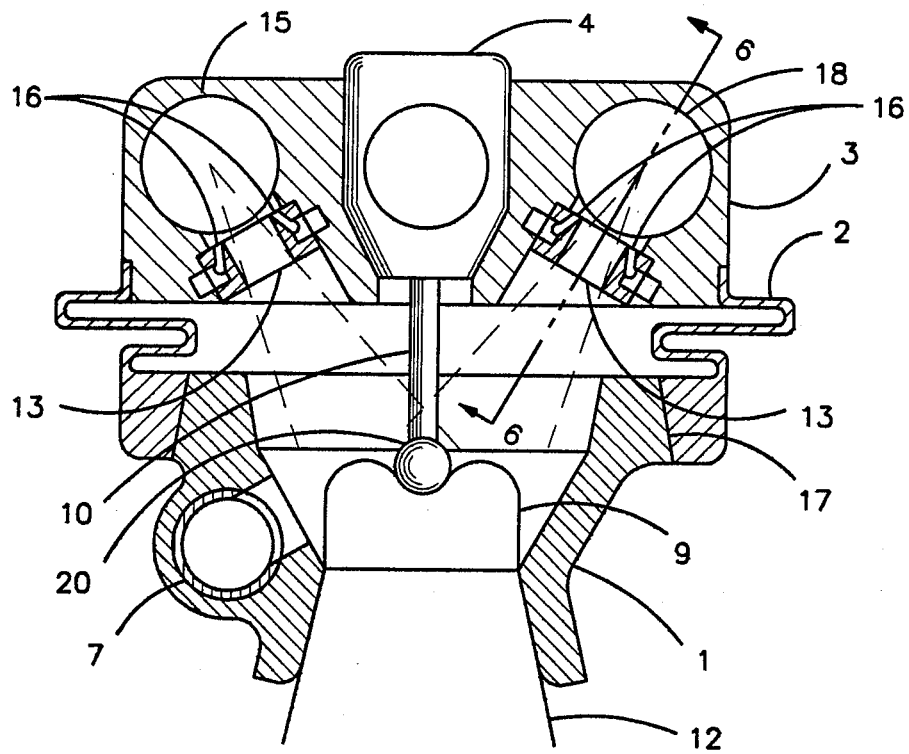
FIG. 2 is a cross section view of the Tooth Isolation Assembly taken from FIG. 4 as shown by 2—2.

Referring to FIG. 2, a cross section of the Tooth Isolation Assembly taken from FIG. 4 as shown by 2—2. Cap 1 fits over the tooth 9 and seals against the gums 12 and adjacent teeth. Bellows 2 is attached to manifold 3 and mated to cap 1 by means of tapered seal 17. Dental handpiece 4 with drill 10 is fitted to manifold 3. The assembled cap 1, bellows 2 and manifold 3 isolate the tooth 9 from the patient's mouth except for those portions of the gums 12 exposed within the cap 1. The bellows 2 permits free movement of the handpiece 4 and drill 10 for easy access to all surfaces of the tooth 9. Flexible cap hose 7 is attached to a suction pump and flexible manifold hose 8, shown in FIG. 3, is connected to either left hand cavity 15 or right hand cavity 18 and is used to supply makeup fresh air when operation takes place on a lower tooth. When the operation is performed on an upper tooth, cap hose 7 is used to supply makeup fresh air and manifold hose 8 is attached to the suction pump. This interchange of functions is necessary to position the hose attached to the suction pump at the lower side of the isolation assembly so that water used during drilling will be removed with the gaseous breakdown products. Fiber optic cable 5 and right angle mirror 6, shown in FIG. 6, are inserted in right hand cavity 18. These may be interchanged with manifold hose 8 in left hand cavity 15 to permit viewing the opposite side of the tooth. Nozzle rings 13 direct compressed air from tubes 11, shown in FIG. 3 and FIG. 4, through nozzle holes 16 to clear right angle mirror 6 and fiber optic lens 19 of water and debris. Light hand cavity 15 and rh cavity 18 are connected by hole 14, shown in FIG. 6, which furnishes a passageway for gaseous breakdown products, water and debris.

Optimum viewing through the fiber optics is provided since the fiber optic cable 5 and the dental handpiece 4 are both attached to the manifold 3 and consequently move as a unit. Thus, the field of view may be set to encompass tip 20 of drill 10 and as drill 10 is moved, the fiber optic field of view follows tip 20.

OPERATION OF INVENTION

The Tooth Isolation Assembly is simple to install and use. The Cap 1 is installed over the tooth as a single piece so that none of the other parts interfere with the dentist's view during this operation. Next, the balance of the Tooth Isolation Assembly, bellows 2, manifold 3 with attached Fiber Optic Viewing and Illumination system, manifold hose 8, cap hose 7, tubes 11 and handpiece 4 are installed as a unit over the cap 1 and held in place by means of the simple tapered seal 17. These may be easily removed at any time for clearing debris or direct visual inspection of the tooth and subsequent reinstallation. The drilling operation takes place after the suction pump and air jets are activated.

CONCLUSION AND SCOPE OF INVENTION

Thus the reader will see that the invention is a simple, easy to use, low cost practical device. It fulfills a need to isolate both the patient and the dentist from the breakdown products of tooth drilling operations. This is especially important for the removal of amalgam fillings which is accompanied by the generation of mercury vapor, one of the most toxic substances known. The invention provides a method to isolate the patient and dentist from these breakdown products more effectively than any of the methods currently in use.

The isolation system can be produced at low cost because it is capable of being adapted to existing dental handpieces which are inherently expensive. Thus, the dentist may continue using the handpieces which he currently owns.

While the above description contains many specificities, these should not be construed as limitations on the scope of the invention, but rather as an exemplification of one preferred embodiment thereof. Accordingly, the scope of the invention should be determined not by the embodiment illustrated, but by the appended claims and their legal equivalents.

I claim:

1. In combination, a means for isolating both a patient and
a dentist from breakdown products of tooth drilling operations comprising:
   a. a cap portion which fits over and seals with a tooth and its associated gum portion;
   b. a manifold portion attached to and positioned adjacent to said cap portion;
   c. a flexible bellows portion positioned between and interconnecting and sealing to said cap portion and said manifold portion to provide a space therebetween, said bellows allowing free motion of said manifold portion relative to said cap portion;
   d. a dental handpiece and drill attached and sealed to said manifold;
   e. a fiber optic viewing and illumination system attached and sealed to said manifold and arranged to afford a view of the tip of said drill and a portion of said tooth;
   f. a suction pump for removing said breakdown products and water associated with drilling through a tube attached to said manifold, said breakdown products and said water replaced with fresh air supplied through a separate tube connected to said manifold;
   g. one or more air jets supplied from a compressed air source for removing water and debris from said fiber optic viewing and illumination system optical surfaces.

* * * * *